United States Patent [19]

Nichols et al.

[11] Patent Number: 4,987,244
[45] Date of Patent: Jan. 22, 1991

[54] ORGANOTIN CATALYSTS FOR USE IN POLYURETHANE SYSTEMS

[75] Inventors: James D. Nichols; John B. Dickenson, both of Fogelsville, Pa.

[73] Assignee: Air Products and Chemicals, Inc., Allentown, Pa.

[21] Appl. No.: 405,700

[22] Filed: Sep. 11, 1989

[51] Int. Cl.$^5$ .............................................. C07F 7/22
[52] U.S. Cl. ........................................ 556/89; 556/90
[58] Field of Search .................................. 556/89, 90

[56] References Cited

U.S. PATENT DOCUMENTS

| | | | |
|---|---|---|---|
| 3,392,128 | 7/1968 | Hostetler et al. | 260/22 |
| 3,582,501 | 6/1971 | Hostetler et al. | 260/2.5 |
| 3,836,488 | 9/1974 | Pruitt et al. | 260/2.5 |
| 3,922,253 | 12/1975 | Jerabek et al. | 260/77.5 |
| 3,980,579 | 9/1976 | Syrop et al. | 252/182 |
| 4,031,050 | 6/1977 | Jerabek | 260/29.2 |
| 4,119,585 | 10/1978 | Kenney et al. | 521/115 |
| 4,254,017 | 11/1978 | Dworkin et al. | 260/45.75 |
| 4,286,073 | 8/1981 | Coe | 521/126 |
| 4,314,934 | 2/1982 | Smith et al. | 260/45.75 |
| 4,816,593 | 3/1989 | Modi et al. | 556/89 |

FOREIGN PATENT DOCUMENTS 0059632  8/1982  European Pat. Off. .

OTHER PUBLICATIONS

Bates, Paul A., Hursthouse, Michael B., "The Structure of 2,2-Dialkyl-1,3,2-Oxathiastannolanes", *Journal of Organometallic Chemistry*, 325 (1987), 129–139.

Yokoo, Makoto, "Tetraalkyldistannoxanes as Catalysts for Urethane Formation", '*Polymer Letters*', vol. 5, pp. 57–63 (1967).

Primary Examiner—Maurice J. Welsh
Attorney, Agent, or Firm—Michael Leach; James C. Simmons; William F. Marsh

[57] ABSTRACT

Useful as catalysts for the reaction of a polyisocyanate or a partially blocked polyisocyanate with a hydroxy-containing compound are organotins of the formula

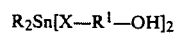

$$R_2Sn[X-R^1-OH]_2$$

where
  R is a $C_1$–$C_8$ alkyl or an aryl group,
  $R^1$ is a $C_2$–$C_9$ divalent hydrocarbyl group which may contain a hydroxyl substituent, and
  X is a linking group which may be —S— or —$O_2$C—.

16 Claims, No Drawings

ORGANOTIN CATALYSTS FOR USE IN POLYURETHANE SYSTEMS

TECHNICAL FIELD

The present invention relates to catalyst compositions for curing polymeric compositions. More particularly, this invention relates to compositions for catalyzing the curing of polymer compositions containing hydroxyl and isocyanate groups.

BACKGROUND OF THE INVENTION

The preparation of polyurethane coatings by reacting organic isocyanates with compounds, especially polyols, containing reactive hydrogen atoms, as determined by the Zerewittenoff reaction, is well-known in the art. These reactions are conventionally carried out in the presence of tertiary amine Catalysts and/or organotin catalysts.

One well-known method for curing polymer compositions is to react a polymer containing pendant hydroxyl groups with a blocked polyfunctional isocyanate. Alternatively, both hydroxyl and blocked isocyanate groups can be present on the same polymer. An isocyanate group can be blocked by reacting it with an active hydrogen-containing compound, such as an alcohol or phenol. When a polymer composition containing hydroxyl and blocked isocyanate groups is heated to above 100° C., the blocking reaction reverses, freeing the isocyanate groups which then react with the hydroxyl groups to form a crosslinked structure.

The use of organic and inorganic tin compounds to cure coating compositions containing hydroxyl and blocked isocyanate groups is disclosed in GB A 994,348. The preferred tin compounds include stannous octoate, stannic chloride, butyltin trichloride, dibutyltin dilaurate, di(2-ethylhexyl) tin oxide and dibutyltin dibutoxide.

The use of blocked isocyanate groups to cure coatings formed from aqueous dispersions of certain hydroxyl-containing polymers is disclosed in U.S. Pat. No. 4,031,050. The polymers are reaction products of an epoxide-containing polymer and a primary and/or secondary amine. This patent discloses that catalysts conventionally employed for the reaction between isocyanates and hydroxyl-containing compounds to form urethane groups may be required, depending upon the reagent employed to form the blocked isocyanate.

Inorganic and organic tin compounds are among the most effective catalysts for the reaction of isocyanates with hydroxyl compounds, particularly alcohols and polyols. Tin compounds frequently employed for this purpose include stannous 2-ethylhexanoate (also referred to as stannous octoate), dibutyltin dilaurate. dibutyltin-bis(dodecyl mercaptan) and dibutyltin oxide (DBTO). Other typical organotin compounds employed or proposed for use as catalysts or co-catalysts in urethane-forming reactions are disclosed for example, in U.S. Pat. Nos. 3,582,501; 3,836,488; 4,119,585. U.S. Pat. No. 3,392,128 discloses the use of dibutyltin sulfonamide and U.S. Pat. No. 3,980,579 discloses a number of dialkyltin thio carboxylates.

Though organotin compounds that are used extensively in polyurethane coatings are effective, there are serious problems associated with the use of these materials. Most currently used organotin compounds are volatile, thus presenting problems regarding atmospheric emissions of toxic materials. There is also the need for hydrolytically stable and system compatible catalysts that can be employed with one component, water-based, urethane emulsions coating systems.

For example, the use of organotin compounds in polyurethane formulations results in these organotin compounds being hydrolyzed in the presence of water with resulting decrease in catalytic activity and system compatibility. The problem is particularly evident in cationic electro-depositable (CED) compositions in which the aqueous coating compositions comprise the reaction product of a partially blocked organic polyisocyanate, an amine adduct of an epoxy group-containing resin and a catalyst for urethane formation. (See U.S. Pat. No. 3,922,253).

Tin oxides are frequently used with polyurethane emulsion coatings. However, there are the same two major problems associated with their use; namely, poor emulsion stability and volatility.

U.S. Pat. No. 4,286,073 discloses hydrolytically stable premix compositions for preparation of urethane foams employing as the organotin catalyst a di- or trialkyltin sulfonate.

EP No. 059.632 B discloses compositions for catalyzing the reaction between blocked isocyanate groups and hydroxyl groups bonded to organic molecules, the compositions comprising a tin-containing urethane catalyst and a metal compound, which is a salt or chelated coordination complex of copper II, zinc II, nickel II, iron II, cobalt II, or vanadium II.

U.S. Pat. No. 3,980,579 discloses a catalytically stabilized polyol composition for use in the preparation of polyurethane foam which comprises a halogen-containing polyol, an amine catalyst and a sulfur-containing organotin compound.

U.S. Pat. No. 4,254,017 discloses organotin compounds containing at least one sulfur atom that is bonded exclusively to tin or to tin and hydrogen. The compounds are derivatives of mercaptoalkanols, which are present as the free alcohols, as esters of polycarboxylic acids, esters of acids containing specified non-metallic elements or as alkoxides of specified metallic elements. The compounds are effective catalysts for a variety of reactions and impart each stability to halogen-containing resins.

U.S. Pat. No. 4,314,934 discloses compositions which are effective in stabilizing polymers against the deteriorative effects of heat comprising (1) an organic tin compound or a mixture of organic tin compounds and (2) an organic compounds or mixture of organic compounds having an aromatic ring which is substituted with hydroxy and mercapto groups ortho to each other.

U.S. Pat. No. 4,816,593 discloses heterocyclic, mono-organotin compounds useful as stabilizers for polyvinyl chloride.

M. Yokoo, et al., *POLYMER LETTERS*. vol. 5, pp. 57–63 (1967) discloses tetraalkyldistannoxanes as catalysts for urethane formation.

P. A. Bates, et al., *Journal of Organometallic Chemistry*, 325, pp. 129–139 (1987) discloses 2,2-dialkyl-1,3,2-oxathiastannolanes.

SUMMARY OF THE INVENTION

The present invention provides organotin compounds of the following general formula:

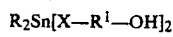

where

R is a $C_1$–$C_8$ alkyl or an aryl group, $R^1$ is a $C_2$–$C_9$ divalent hydrocarbyl group which may contain a hydroxyl substituent, and X is a linking group which may be —S— or —$O_2$C—. which are useful as catalysts for the reaction of an isocyanate or blocked isocyanate functionality with a reactive hydrogen-containing compound in polyurethane coating and foam compositions.

The use of the compounds of this invention can solve the problems of catalyst volatility and emulsion stability by becoming chemically bound via the hydroxy functionality to one or more of the components contained in the polyurethane coating formulation.

In addition to effectively catalyzing the OH/NCO reaction, the organotin compounds are either hydrolytically stable or their susceptibility to hydrolysis is lessened when chemically bound to the coating resin component.

Another embodiment of the invention is a polyurethane coating composition comprising a polyisocyanate, a polyol and an organotin compound of the above general formula.

Yet another embodiment is a cationic electrodepositable composition comprising an at least partially-blocked polyisocyanate, an amine adduct of an epoxy group-containing resin and an organotin compound of the invention.

A further embodiment of the invention is a polyurethane foam composition comprising polyisocyanate, polyol, an organotin compound of the above general formula, optionally an amine catalyst, and a blowing agent such as water or halocarbon (chlorofluorocarbon).

DETAILED DESCRIPTION OF THE INVENTION

The organotin catalysts of the invention are of either of the following two formulas:

where

R is a $C_1$–$C_8$ alkyl group, preferably n-butyl or octyl, or an aryl group, preferably phenyl; and $R^1$ is a $C_2$–$C_9$ divalent hydrocarbyl group, for example, alkylene, arylene and alkarylene, preferably ethylene, propylene, butylene, phenylene [—$C_6H_4$—], —$CH_2$—$C_6H_4$—, —$CH_2CH_2$—$C_6H_4$—, and —$CH_2CH_2CH_2C_6H_4$—, which hydrocarbyl group may also contain a hydroxyl substituent.

When the linking group X is —S—, it is preferred that $R^1$ be a hydroxy substituted $C_3$–$C_5$ alkylene group such as —$CH_2$—CH(OH)—$CH_2$. When the linking group X is —$O_2$C—, it is preferred that $R^1$ be —($CH_2$)$_n$—$C_6H_4$— where n=0–3.

Specific compounds include:
dibutyltin bis-(2,3-dihydroxypropylmercaptide)
dibutyltin bis-(2-hydroxyethylmercaptide)
dibutyltin bis-(4-hydroxyphenylmercaptide)
dioctyltin bis-(2-hydroxyethylmercaptide)
dioctyltin bis-(4-hydroxybutylmercaptide)
dibutyltin bis-(4-hydroxyphenylacetate)
dibutyltin bis-[3-(4-hydroxyphenyl)propionate]
dioctyltin bis-(4-hydroxyphenylacetate)
dioctyltin bis-(3-hydroxybutyrate)
diphenyltin bis-(3-hydroxybutyrate)

A general procedure for preparing the diorganotin bis-carboxylates and diorganotin bis-mercaptides would involve charging a mixture of diorganotin oxide ($R_2$SnO). the appropriate carboxylic acid (HOR$^1$-$CO_2$H) or mercaptan (HOR$^1$SH), and a solvent such as toluene to a reaction vessel and heating the reaction mixture to reflux temperature until all the water of reaction has been removed by distillation. The organic solvent can then be evaporated to afford essentially quantitative product yields of the diorganotin bis-carboxylate or bis-mercaptide.

A catalytically effective amount of the diorganotin catalyst of the invention is used in a polyurethane formulation comprising polyisocyanate and a polyether or polyester polyol. Specifically, suitable amounts of the catalyst may range from about 0.1 to 2 parts, preferably 0.25 to 1 parts, per 100 parts by wt polyol in the polyurethane coating or foam formulation.

Examples of a suitable polyisocyanates are hexamethylene diisocyanate, phenylenediisocyanate, toluenediisocyanate, and 4,4'-diphenylmethanediisocyanate. Especially suitable are the 2,4- and 2,6-toluenediisocyanates individually or together as their commercially available mixtures. Other suitable mixtures of diisocyanates are those known commercially as "crude MDI", also known as PAPI, which contain about 60% of 4,4'-diphenylmethanediisocyanate along with other isomeric and analogous higher polyisocyanates. Also suitable are "prepolymers" of these polyisocyanates comprising a partially prereacted mixture of polyisocyanates and of polyether or polyester polyol.

Illustrative of suitable polyols as a component of the polyurethane coating compositions catalyzed by the diorganotin compounds of the invention are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols, for example, among others, ethylene glycol, propylene glycol, 1,3-butane diol, 1,4-butane diol, 1,6-hexane diol, neopentyl glycol, diethylene glycol, dipropylene glycol, pentaerythritol, gycerol, diglycerol, trimethylol propane, hexane diol and like low molecular weight polyols.

Useful polyester polyols include those produced by reacting a carboxylic acid with an excess of a diol; for example, adipic acid with ethylene glycol or butane diol, or reacting a lactone with an excess of a diol, such as caprolactone and propylene glycol.

Other typical components in a polyurethane foam composition include a blowing agent such as water and/or halocarbon and optionally cell stabilizer, crossliner linker and amine catalyst.

Other typical components found in polyurethane coating compositions include emulsifier, pigment and solvent.

A general water-based polyurethane coating formulation containing a diorganotin compound of the invention would comprise the following: polyol, blocked polyisocyanate (TDI and/or MDI), organic or inorganic acid, crosslinker, pigment and water.

A cationic electrodepositable (CED) polyurethane coating composition would comprise an aqueous dispersion of a cationic resin and an at least partially blocked polyisocyanate compound, a tin catalyst according to the present invention and, optionally, pigment and a coalescing solvent. The cationic resin is usually the reaction product of a polyepoxide resin with a monoamine, particularly tertiary and secondary amines which desirably contain hydroxyl functionality. The polyepoxide resin may also be reacted with the partially blocked organic polyisocyanate and/or a polyester polyol or polyether polyol prior to or after reaction with the monoamine.

A catalytically effective amount of the diorganotin catalyst of the invention is used in the CED polyurethane coating composition. Suitable amounts of the catalyst may range from about 0.5 to 5 parts per 100 parts by wt resin.

The polyepoxides, which can be used in the CED compositions are polymers having a 1,2-epoxy equivalency greater than 1 and preferably about 2. The preferred polyepoxides are polyglycidyl ethers of cyclic polyols. Particularly preferred are polyglycidyl ethers of polyhydric phenols, such as bis-phenol A. The polyepoxides have a molecular weight of at least 200 and preferably within a range of 200-2000 and, more preferably, about 340-2000.

Examples of suitable polyester polyols are those which are formed by reacting a dicarboxylic acid or acid anhydride such as adipic acid, succinic acid or anhydride with a polyol such as butanediol, hexanediol or polyethylene glycol. Commercially available products are sold under the trademarks Mobay E-365 and E-604.

Examples of suitable polyether polyols are those which are formed by reacting a cyclic polyol with ethylene oxide or optionally with a mixture of ethylene oxide and an alkylene oxide having 3 to 4 carbon atoms in the alkylene chain. Examples of the cyclic polyols which can be used are polyhydric phenols and cycloaliphatic polyols. The cyclic polyol-alkylene oxide condensate is preferably difunctional or trifunctional and the equivalent ratio of cyclic polyol to alkylene oxide should be within the range of 1:3 to 20.

The partially blocked organic polyisocyanate which may be employed in preparing the CED compositions may be any polyisocyanate where a portion of the isocyanate groups have been reacted with a compound so that the resultant capped isocyanate portion is stable to hydroxyl or amine groups at room temperature but reactive with hydroxyl or amine groups at elevated temperatures, usually between about 200° and 600° F.

In the preparation of the partially blocked polyisocyanate, any suitable organic polyisocyanate may be used. In addition, the organic polyisocyanate may be a prepolymer derived from a polyol, including polyether polyol or polyester polyol, which are reacted with excess polyisocyanate to form isocyanate-terminated prepolymers. Any suitable aliphatic, cycloaliphatic or aromatic alkyl monoalcohol may be used as a blocking agent.

The electrodepositable compositions may also contain a coalescing solvent, a pigment composition of any of the conventional types, plasticizers, surfactants or wetting agents.

For more information and detail about the components that compose cationic electrodepositable compositions, the relative amounts of these components and the method of their preparation and use, see U.S. Pat. Nos. 3,922,253; 4,104,147 and 4,419,467 which are hereby incorporated by reference.

EXAMPLE 1

This example shows the preparation of dibutyltin bis-(4-hydroxyphenylacetate). A mixture of 24.9 g (0.10 moles) dibutyltin oxide, 30.4 g (0.20 mole) 4-hydroxyphenylacetic acid, and 300 ml toluene were charged to a 3-necked round bottom flask equipped with a stirrer, thermocouple or thermometer, and condenser with a DEAN-STARK water trap, and heated at reflux temperature until all the water of reaction was collected in the trap. The toluene was removed using a flash evaporator to yield 53 g (99%) of dibutyltin bis-(4-hydroxyphenyl acetate) having a melting point of 121°-126° C.

EXAMPLE 2

Following the procedure of Example 1, dibutyltin oxide was reacted with 33.2 g (0.2 mole) 3-(4-hydroxyphenyl)propionic acid to yield 56 g of dibutyltin bis-(3-(4-hydroxyphenyl)propionatel, a white crystalline material melting at 48°-50° C.

EXAMPLE 3

A mixture of 24.9 g (0.10 mole) dibutyltin dioxide, 21.6 g (0.20 mole) 3-mercapto-1,2-propanediol and 300 ml toluene were reacted as described in Example 1. Removal of the toluene yielded 44.5 g (99.5%) of dibutyltin bis-(2,3-dihydroxypropylmercaptide), $(C_4H_9)_2Sn[SCH_2CH(OH)CH_2OH]_2$. The product was a straw-colored viscous liquid.

EXAMPLE 4

The procedure of Example 3 was followed, except that 15.6 g (0.2 mole) 2-mercaptoethanol, was used to yield 38 g (98%) of dibutyltin bis-(2-hydroxyethylmercaptide) $(C_4H_9)_2Sn[SCH_2CH_2OH]_2$. The product was a light yellow liquid.

EXAMPLE 5

The procedure of Example 3 was followed, except that 25.2 g (0.20 mole) 4-mercaptophenol was used to provide 46 g (95%) of dibutyltin bis-(4-hydroxyphenylmercaptide), $(C_4H_9)_2Sn[SC_6H_4OH]_2$, which was an amber liquid.

EXAMPLE 6

The organotin catalysts of Examples 1-5 were evaluated as catalysts for the isocyanate-hydroxyl reaction according to the following gelation test. A solution of the dialkyltin compound (0.5 mole%) in 9 g solvent (dioxane or D methylisobutylketone) was prepared. To this solution was added 159 g of a poly(oxyalkylene)-triol (Mobay Multranol E-9143, OH number =35), and after thoroughly mixing, 8.5 g toluene diisocyanate (80/20 ratio of 2,4/2,6 isomer mixture) was added to the catalyst/triol solution and mixed for 30 seconds. A small test tube was filled with the mixture, sealed and immediately placed in a constant temperature bath (25°, 50° or 70° C.). The time required to mix, fill the test tube, seal it and place it in the bath was 1.0 min. for each test. The gel time was measured from the instant the tube was placed in the bath, and was taken as the time when the mixture would no longer visibly flow in the inverted tube. The gelation time was interpreted as a measure of the speed of the isocyanate-hydroxyl reaction in the mixture.

Table 1 shows the results of the gelation test.

TABLE 1

| Dialkyltin Compound | Gel Point (Minutes) | | |
|---|---|---|---|
| | 25° C. | 50° C. | 70° C. |
| 1 | 16.3 | | 2.4 |
| 2 | 12.9 | | 2.3 |
| 3 | 12.9 | 4.6 | |
| 4 | 14.0 | 5.2 | |
| 5 | 25.3 | 8.3 | |
| DBTO | >240 | 20 | 4.5 |
| T-1* | 13.0 | 5.5 | 2.4 |

*T-1 = dibutyltin diacetate

The data in Table 1 shows that the dialkyltin compounds 1-5 all catalyze the isocyanate/hydroxyl reaction.

EXAMPLE 7

Each of the dialkyltin compounds 1-5 were evaluated for hydrolysis stability. The test conditions simulate the conditions encountered by the catalyst in an aqueous polyurethane coating bath such as a CED bath.

5.0 g of a 10% solution of the dialkyltin compound in toluene was added to a test tube containing 20 ml dilute acetic acid, pH 6.5. The contents, which form two immiscible phases, were mixed by inverting the tube several times and then allowed to stand at ambient temperature. Hydrolytic stability under these conditions was measured by the time (days) required for the appearance of a precipitate (the hydrolysis product which is insoluble in both phases) at the toluene-acetic acid interface. The results of this hydrolysis stability test are shown in Table 2.

TABLE 2

| Dialkyltin Compound | Precipitate | Time (days) |
|---|---|---|
| 1 | Yes | 3 |
| 2 | Yes | 62 |
| 3 | No | >200 |
| 4 | No | >200 |
| 5 | No | >200 |
| T-1 | Yes | <1 |

The hydrolytic stability data shows that each of the dialkyltin compounds according to the invention demonstrated the improved hydrolytic stability compared to T-1 catalyst. Compounds 3-5 did not produce a precipitate after 200 days of testing.

Statement of Industrial Application

The diorganotin compounds of the present invention are useful as urethane catalysts in aqueous polyurethane coating and foam compositions, in particular, cationic electrodepositable polyurethane compositions.

2901p

What is claimed:

1. A compound of the formula $$R_2Sn[X-R^1-OH]_2$$

where
R is a $C_1-C_8$ alkyl or an aryl group,
$R^1$ is a $C_2-C_9$ divalent hydrocarbyl group which may be substituted with a hydroxyl group, and
X is $-S-$ or $-O_2C-$, provided that when X is $-S-$ and $R^1$ is an alkylene group, $R^1$ contains a hydroxyl group.

2. The compound of claim 1 in which R is butyl or octyl.

3. The compound of claim 1 in which X is $-S-$.

4. The compound of claim 3 in which $R^1$ is a hydroxy substituted $C_3-C_5$ alkylene.

5. The compound of claim 3 in which $R^1$ is $-CH_2-CH(OH)-CH_2-$.

6. The compound of claim 1 in which X is $-O_2C-$.

7. The compound of claim 6 in which $R^1$ is $-(CH_2)_n-C_6H_4-$ where n=0-3.

8. The compound of claim 7 in which $R^1$ is $-(CH_2)_2-C_6H_4-$.

9. The compound of claim 7 in which $R^1$ is $-CH_2-C_6H_4-$.

10. A compound of the formula $$R_2Sn[S-R^1-OH]_2$$

where
R is butyl or octyl and
$R^1$ is a hydroxy substituted $C_3-C_5$ alkylene.

11. The compound of claim 10 in which $R^1$ is $-CH_2-CH(OH)-CH_2-$.

12. The compound of claim 10 in which R is butyl.

13. A compound of the formula $$R_2Sn[O_2C-R^1-OH]_2$$

where
R is butyl or octyl and
$R^1$ is a $C_2-C_9$ divalent hydrocarbyl group.

14. The compound of claim 13 in which is $-(CH_2)_n-C_6H_4-$ where n=0-3.

15. The compound of claim 13 in which $R^1$ is $-CH_2C_6H_4-$.

16. The compound of claim 13 in which $R^1$ is $-CH_2CH_2C_6H_4-$.

* * * * *

UNITED STATES PATENT AND TRADEMARK OFFICE
CERTIFICATE OF CORRECTION

PATENT NO.   :   4,987,244
DATED        :   22 January 1991
INVENTOR(S)  :   James D. Nichols and John B. Dickenson It is certified that error appears in the above-identified patent and that said Letters Patent is hereby corrected as shown below:

In the Claims

Column 8, Line 46, Claim 14.

After the word "which" insert -- $R^1$ --.

Signed and Sealed this

Sixteenth Day of April, 1991

Attest:

Attesting Officer

HARRY F. MANBECK, JR.

Commissioner of Patents and Trademarks